(12) United States Patent
Chan et al.

(10) Patent No.: US 10,646,467 B2
(45) Date of Patent: May 12, 2020

(54) PRODRUG OF GREEN TEA EPIGALLOCATECHIN-3-GALLATE (PRO-EGCG) FOR USE IN THE TREATMENT OF ENDOMETRIOSIS

(71) Applicants: The Hong Kong Polytechnic University, Hong Kong (CN); The Chinese University of Hong Kong, Hong Kong (CN)

(72) Inventors: Tak-Hang Chan, Hong Kong (CN); Chi-Chiu Wang, Hong Kong (CN)

(*) Notice: Subject to any disclaimer, the term of this patent is extended or adjusted under 35 U.S.C. 154(b) by 0 days.

(21) Appl. No.: 16/259,620

(22) Filed: Jan. 28, 2019

(65) Prior Publication Data

US 2019/0151282 A1    May 23, 2019

Related U.S. Application Data

(60) Continuation of application No. 15/628,001, filed on Jun. 20, 2017, now Pat. No. 10,188,629, which is a division of application No. 14/422,642, filed as application No. PCT/CN2013/081900 on Aug. 20, 2013, now Pat. No. 9,713,603.

(60) Provisional application No. 61/684,852, filed on Aug. 20, 2012.

(51) Int. Cl.
*A61K 31/353* (2006.01)
*A61K 9/00* (2006.01)

(52) U.S. Cl.
CPC .......... *A61K 31/353* (2013.01); *A61K 9/0034* (2013.01)

(58) Field of Classification Search
CPC .................................................... A61K 31/353
USPC ......................................................... 514/456
See application file for complete search history.

(56) References Cited

U.S. PATENT DOCUMENTS 9,713,603 B2 *   7/2017   Chan .................... A61K 9/0034
10,188,629 B2 *  1/2019   Chan .................... A61K 9/0034

* cited by examiner

*Primary Examiner* — Nizal S Chandrakumar
(74) *Attorney, Agent, or Firm* — Law Offices of Albert Wai-Kit Chan, PLLC

(57) ABSTRACT

Method of treating endometriosis and related indications, comprising the administration of Pro-EGCG, a synthetic and derivative product of epigallocatechin-3-gallate [(−)-EGCG]. Use of PRO-EGCG in the manufacture of a medicament for treating endometriosis and related indications. Pro-EGCG for use in the treatment of endometriosis and related indications.

17 Claims, 8 Drawing Sheets

PRODRUG OF GREEN TEA EPIGALLOCATECHIN-3-GALLATE (PRO-EGCG) FOR USE IN THE TREATMENT OF ENDOMETRIOSIS

FIELD OF THE INVENTION

The invention relates to the novel application of Pro-EGCG, a synthetic derivative of (−)-epigallocatechin-3-gallate (EGCG) in a method of treating endometriosis and related indications comprising the administration of Pro-EGCG.

The invention also pertains to the use of Pro-EGCG in the manufacture of a medicament for the treatment of endometriosis and related indications, and Pro-EGCG for use in the treatment of endometriosis and related indications.

BACKGROUND OF THE INVENTION

Angiogenesis (the physiological process through which new blood vessels form from pre-existing vessels) has an essential role in development, reproduction and repair. However, pathological angiogenesis occurs not only in tumor formation but also in a range of non-neoplastic diseases that could be classed together as "angiogenesis-dependent diseases" (Carmeliet P and Jain R K (2000) Nature 407, 249-257; Simons M (2005) Circulation 111, 1556-1566).

Endometriosis is a chronic disorder characterized by the implantation of endometrial glands and stroma outside the uterine cavity. Despite different hypotheses regarding the pathogenesis of endometriosis, it is widely accepted that endometriosis is an angiogenesis-dependent disorder and that angiogenesis plays an essential role in the growth and survival of endometriotic lesions (Taylor R N, et al. Ann N Y Acad Sci 2002; 955:89-100).

Endometriotic lesions require new vessel formation to deliver the oxygen and nutrient supply that are essential to the development and progression of endometriosis (Groothuis P G, et al. Angiogenesis 2005; 8:147-56). Dense vascularization is a typical pathological feature of endometriosis. Numerous peritoneal blood vessels can be observed around the endometriotic lesions during laparoscopy, and ectopic endometrium is highly vascularized under histological examination (Nisolle M, et al. Fertil Steril 1993; 59:681-4).

Animal models have confirmed that angiogenesis occurs in endometriosis by demonstrating the development of adjacent blood vessels from the surrounding vasculature into the endometriotic implants (Becker C M, et al. Am J Pathol 2008; 172:534-44; Xu H, et al. Hum Reprod 2009; 24:608-18). Anti-angiogenesis therapy offers a new opportunity for the treatment of endometriosis (Hull M I., et al. J Clin Endocrinol Metab 2003; 88:2889-99).

Current treatments for endometriosis consist of various hormonal therapies aimed at interrupting the cycles of stimulation and bleeding of endometriotic lesions. However, this approach is deemed not very satisfactory (Rice V M. Ann N Y Acad Sci 2002; 955:343-52).

Anti-angiogenesis for the treatment of endometriosis has the potential advantage of lower recurrence rates and less endocrine side effects compared to conventional surgical and hormonal therapies (Xu Wang C C. Endometriosis: Symptoms, Diagnosis and Treatments. Mitchell L A Ed. Nova Science, New York. Chapter 1, pp. 1-40, 2010). Common angiostatic compounds, such as VEGF antibody, TNP-470, endostatin and anginex, have significantly decreased microvessel density in the established endometriosis lesions and significantly inhibited the growth and development of endometriosis (Nap A W, et al. J Clin Endocrinol Metab 2004; 89:1089-95; Dabrosin C, et al. Am J Pathol. 2002; 161:909-18; Yagyu T, et al. J Clin Endocrinol Metab 2005; 90:3017-21). To date, the only clinical trial that has been conducted was on thalidomide (Scarpellini F, et al. Fertil Steril 2002; 78:S87).

Although the results showed promising pain relief in endometriosis patients, thalidomide is a potential teratogen, which prohibits its use in women who want to become pregnant. Furthermore, anti-angiogenic agents could also serve to limit physiological angiogenesis, such as in ovulation and menstruation (Nyberg P, et al. Cancer Res 2005; 65:3967-79). These agents' possible adverse effects on reproductive functions and on offspring must be addressed in this vulnerable population (Klauber N, et al. AGM-1470. Nat Med 1997; 3:443-6; Becker C M, et al. Fertil Steril 2005; 84 Suppl 2:1144-55).

Certain compounds in Tea have been identified as having have various biological benefits. In particular, tea polyphenols are the main chemical constituents of green tea (Graham H N. Preventive Med. 1992; 21:334-50). Specifically, The polyphenols found in green tea which are composed of various kinds of catechin derivatives, mainly catechin (C), epicatechin (EC), gallocatechin (GC), epigallocatechin (ECC), epicatechin-3-gallate (ECG), gallocatechin-3-gallate (GCG) and epigallocatechin-3-gallate (EGCG), and are found to have potent anti-oxidative, anti-mitotic and anti-angiogenic properties (Nagle D C, et al. Phytochemistry 2006; 67:1849-55).

In particular, EGCG is the most abundant catechin and has the most potent biological properties among the other catechins (Lea C H, et al. Chem Ind 1957; 1073-4). The anti-angiogenic activity of EGCG has been widely demonstrated in vitro and in vivo (Cao Y H, et al. Nature 1999; 398:381). In our laboratory, we demonstrated that EGCG suppressed the angiogenesis signaling pathway and inhibited neovascularization and the growth of experimental endometriosis in mice (Xu H, et al. Hum Reprod 2009; 24:608-18; Xu H, et al. Fertil Steril 2011; 96:1021-8).

However, EGCG is notably unstable under physiological conditions and is known to have poor bioavailability (Chen Z, et al. J Agric Food Chem 2001; 49, 477-82), because it is (1) unstable in neutral or slightly alkaline conditions in the intestine and in body fluid; (2) poorly absorbed due to the high hydrophilicity of EGCG; and (3) modified through biotransformation reactions, including methylation, glucuronidation, and sulfate formation (Zhu Q Y, et al. J Agric Food Chem 1997; 45:4624-8).

SUMMARY OF THE INVENTION

It is an object of the invention to provide a more effective therapeutic method for treating endometriosis which seeks to alleviate some of the problems associated with the current treatment methods for endometriosis or provides a potential alternative.

In a first aspect, the present application provides a method of treating endometriosis or a related indication comprising administering to a subject in need thereof an effective amount of Pro-EGCG having the formula:

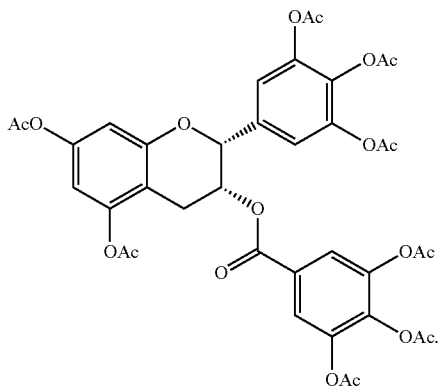 [SMILES: CC(=O)Oc1cc(OC(C)=O)c2c(c1)O[C@H](c1cc(OC(C)=O)c(OC(C)=O)c(OC(C)=O)c1)[C@H](OC(=O)c1cc(OC(C)=O)c(OC(C)=O)c(OC(C)=O)c1)C2]

In a preferred embodiment, the method is a method of treating endometriosis, which may be peritoneal or pelvic endometriosis. In another preferred embodiment, the method is a method of treating adenomyosis.

The method may involve administering Pro-EGCG into the uterine cavity or the vagina of the subject.

In a second aspect, the present invention provides Pro-EGCG having the formula:

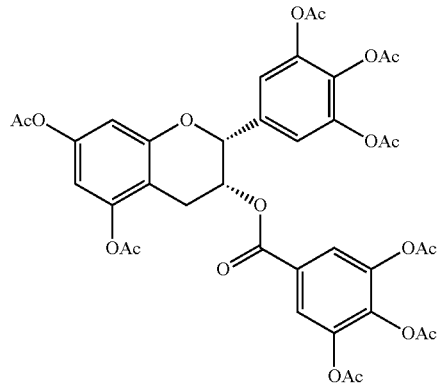 [SMILES: CC(=O)Oc1cc(OC(C)=O)c2c(c1)O[C@H](c1cc(OC(C)=O)c(OC(C)=O)c(OC(C)=O)c1)[C@H](OC(=O)c1cc(OC(C)=O)c(OC(C)=O)c(OC(C)=O)c1)C2]

for use in a method of treating endometriosis or a related indication in a subject in need thereof.

In a preferred embodiment, the Pro-EGCG is used in a method of treating endometriosis, which may be peritoneal or pelvic endometriosis. In another preferred embodiment, the Pro-EGCG is used in a method of treating adenomyosis.

The Pro-EGCG, when for use in a method of treating endometriosis or a related indication in a subject in need thereof, may be administered into the uterine cavity or the vagina of the subject.

In a third aspect, the present invention provides the use of an effective amount of Pro-EGCG having the formula:

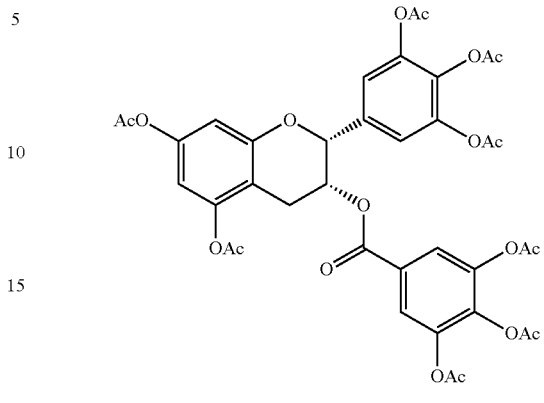

for the manufacture of a medicament for treating endometriosis or a related indication in a subject in need thereof.

In a preferred embodiment, the medicament is for treating endometriosis, which may be peritoneal or pelvic endometriosis. In another preferred embodiment, the medicament is for treating adenomyosis.

The medicament, when used for the treatment of endometriosis or a related indication, is suitable for administration into the uterine cavity or the vagina of the subject.

Figure 3A:
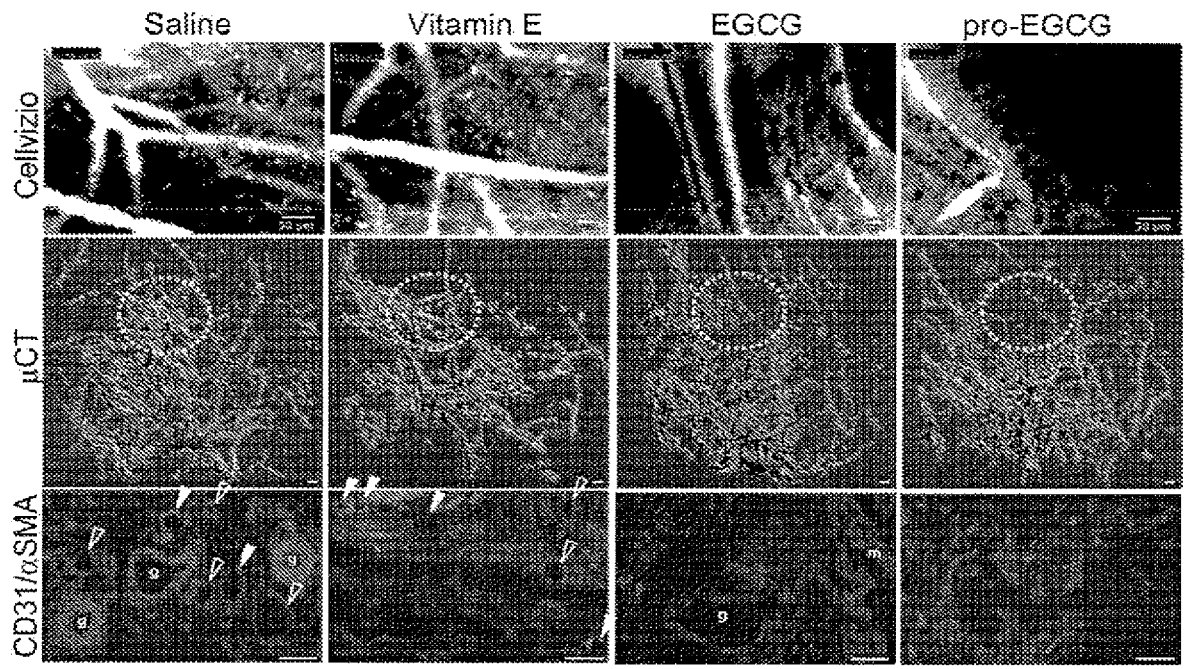
FIG. 3A shows at the upper panels microvessels in the endometriotic implants perfused with FITC-Dextran and captured by Cellvizio (white colour); at the middle panel microvessel architectures surrounding the lesions and within the lesions were perfused with microfil contrast medium and captured by μCT (yellow dots); and at the lower panels microvessels in the endometriotic lesions determined by specific anti-mouse antibodies antibodies CD31 for endothelial cells in red, αSMA for smooth muscles in green, and DAPI for nuclei in blue. New microvessels are CD31- positively and αSMA-negatively stained (closed arrows). g: endometrial glands; c: endometrial cyst-like structures; m: abdominal muscle. Representative images in different groups are shown. Scale bars: 10 μm.
Figure 3B:
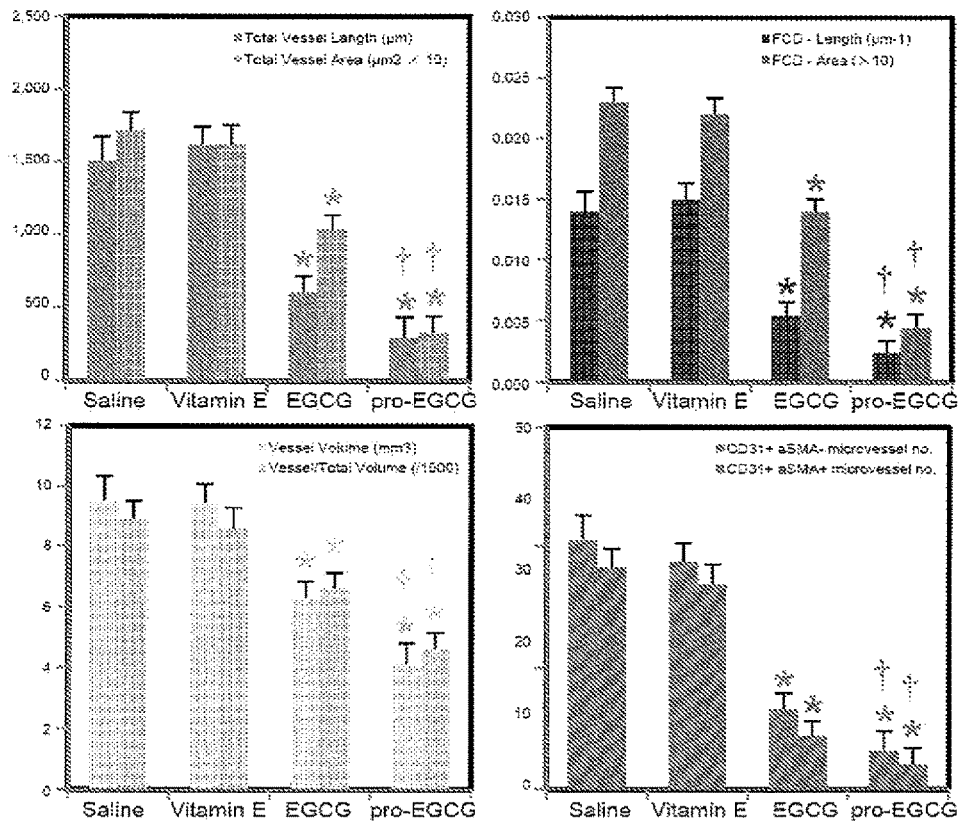

FIG. 3B shows bar charts of the lesion microvessel parameters in different groups. Mean±SEM, Student's T test, *P<0.05 compared with saline group; †P<0.05 compared with EGCG group.

Figure 4A:
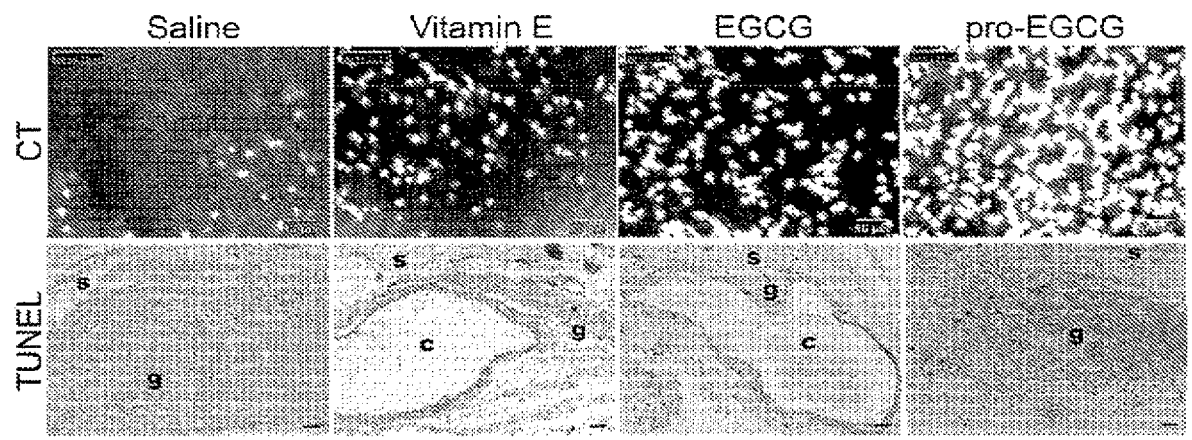

FIG. 4A shows at the upper panels apoptotic cells in the endometriotic implants labeled with YO-PRO®-1 iodide and captured (white colour); and at lower panels apoptotic cells in the endometriotic lesions determined by TUNEL staining (dark brown stains). s: skin and subcutaneous layers, g: endometrial glands; c: endometrial cyst-like structures. Representative images in different groups are shown. Scale bars: 50 μm.

Figure 4B:
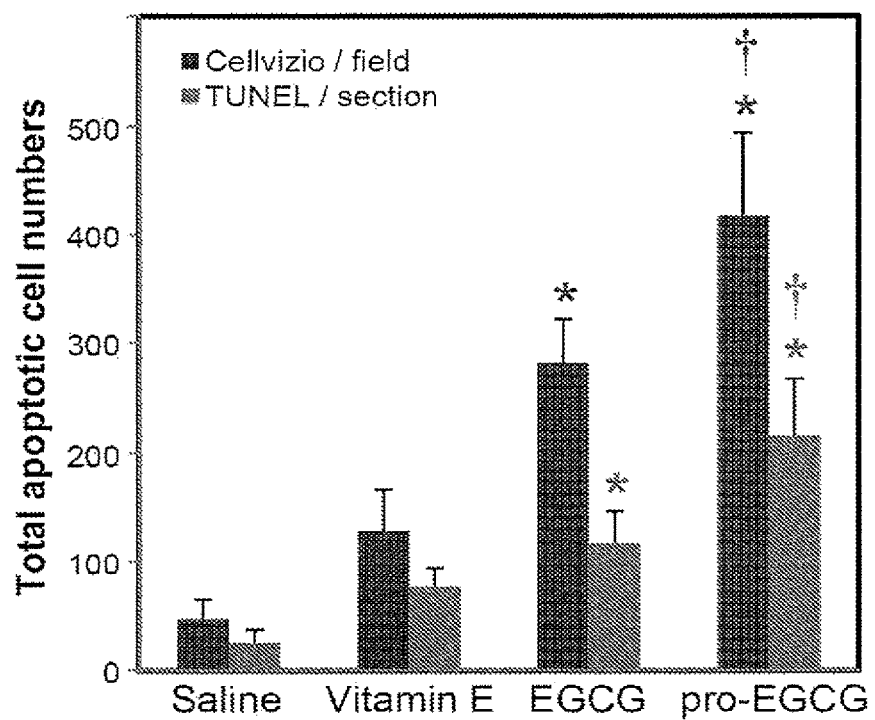

FIG. 4B Bar charts of the lesion apoptotic cells by Cellvizio imaging and TUNEL staining in different groups. Mean±SEM, Student's T test, *P<0.05 compared with saline group; †P<0.05 compared with EGCG group.

Figure 5A:
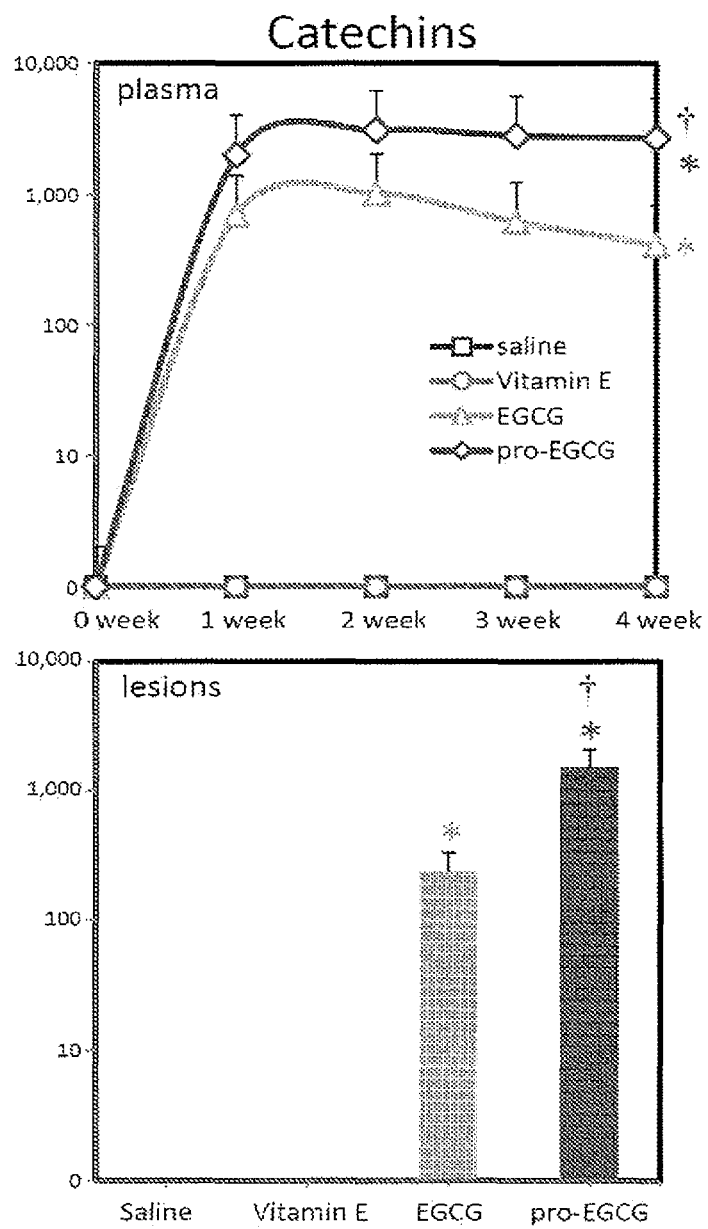
Figure 5B:
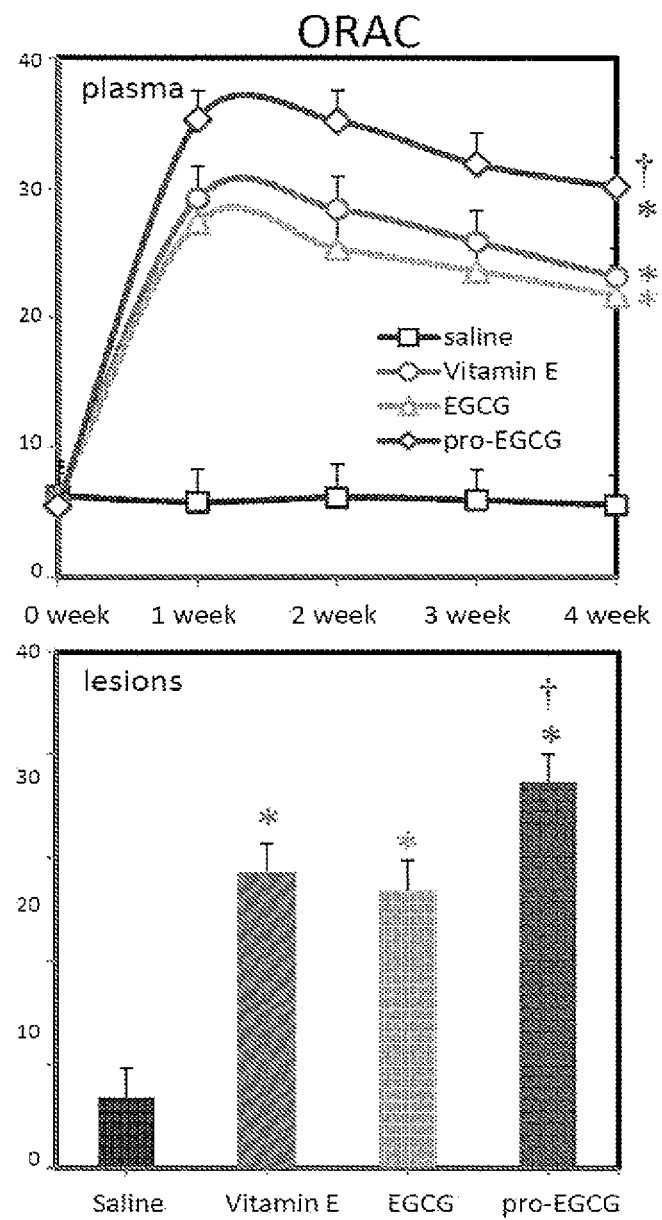
Figure 5C:
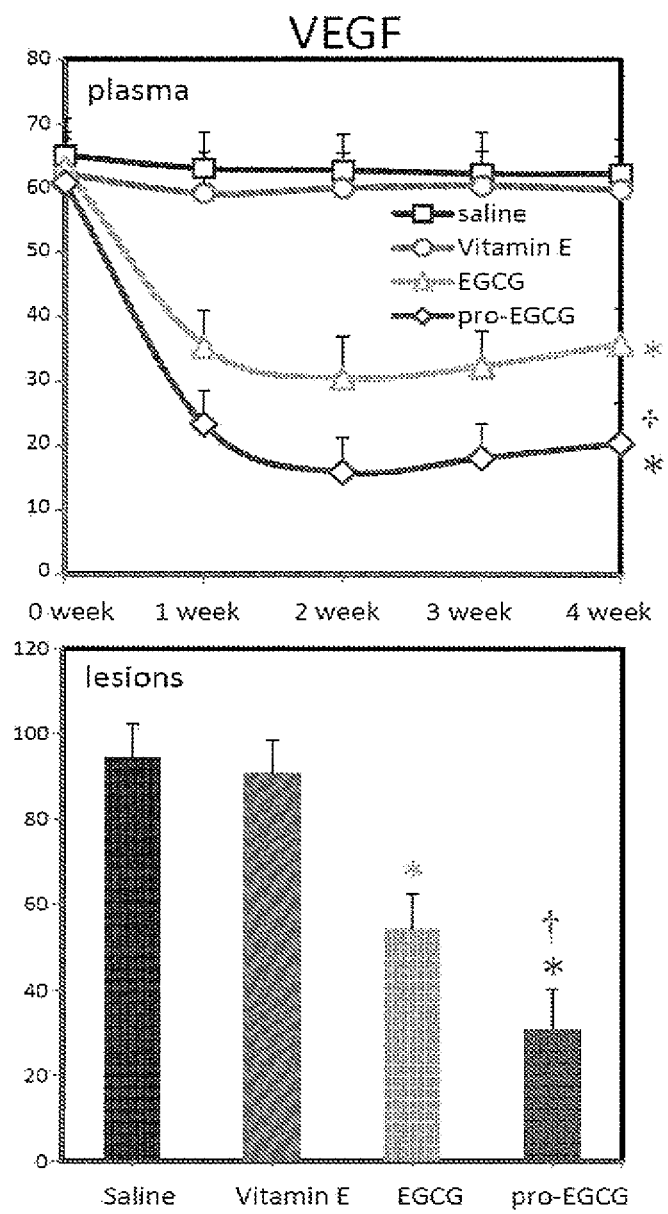

FIG. 5A-5C show at the upper panels show the changes of (A) corresponding EGCG and pro-EGCG concentrations (pmol/ml), (B) oxygen radical absorbance capacity (ORAC, mM Trolox-equiv/ml) and (C) vascular endothelial growth factor (VEGF, pg/ml) concentrations in plasma during intervention. Mean±SEM, On-way ANOVA and multiple comparisons by post hoc Bonferroni test, *P<0.05 compared with saline group; †P<0.05 compared with EGCG group; and at the lower panels show the final EGCG and pro-EGCG concentrations (pmol/mg), ORAC (mM Trolox-equiv/mg) and VEGF concentrations (pg/mg) in the lesions after intervention. Mean±SEM, Student's T test, *P<0.05 compared with saline group; †P<0.05 compared with EGCG group.

Figure 6A:
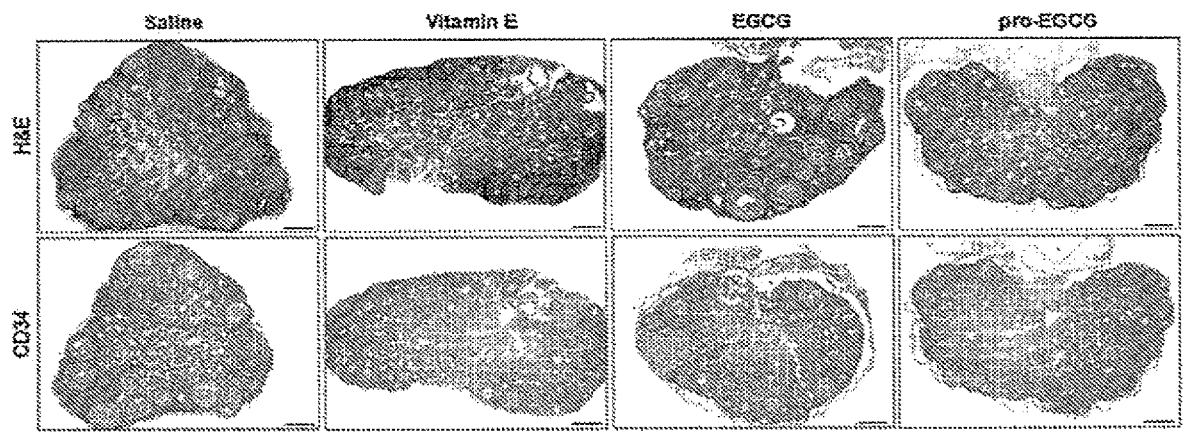
Figure 6B:
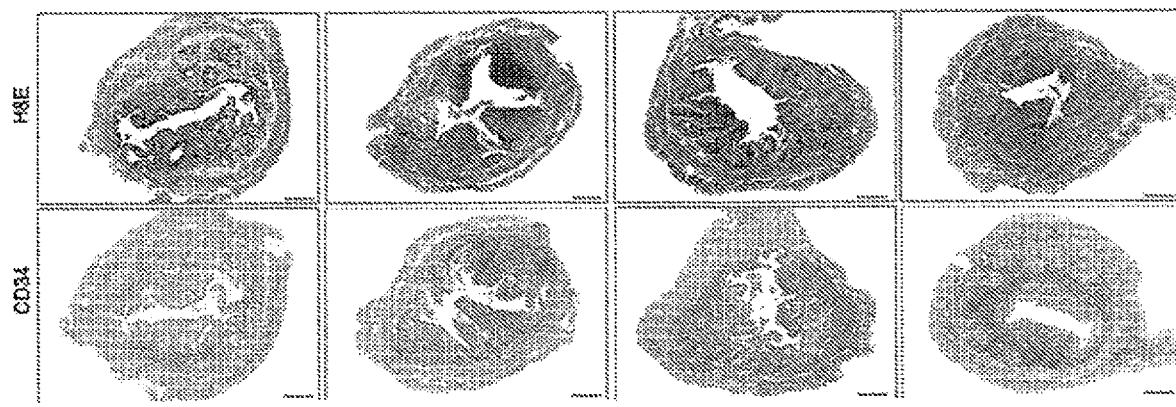

FIG. 6A-6B shows ovarian follicles and endometrial glands determined by H&E staining and microvessels in ovarian and endometrial stroma determined by anti-mouse CD34 immunostaining in ovaries (upper panels) and uterus (lower panels). Representative images in different groups are shown. Scale bars: 0.5 mm.

DETAILED DESCRIPTION OF THE INVENTION

"Pro-EGCG" as used herein refers to a synthetic derivative of EGCG, obtained by acetylation of EGCG, which can act as a prodrug of EGCG (pro-EGCG). It can also be referred to as (-)-EGCG octaacetate.

Pro-EGCG as defined by the following chemical formula:

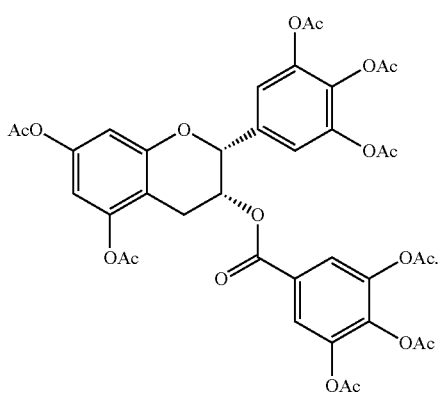 [SMILES: CC(=O)Oc1cc(OC(C)=O)c2c(c1)O[C@H](c1cc(OC(C)=O)c(OC(C)=O)c(OC(C)=O)c1)[C@H](OC(=O)c1cc(OC(C)=O)c(OC(C)=O)c(OC(C)=O)c1)C2]

Pro-EGCG is a protected EGCG analogue created by the acetylation of the reactive hydroxyl groups, which prevents generation of the more reactive phenoxide anions and radicals for dimerization and metabolism (Chen Z, et al. J Agric Food Chem 2001; 49, 477-82). In addition, pro-EGCG remains biologically inactive until it is deacetylated by esterases and converted into its parent EGCG compound in cells (Lam W H, et al. Bioorg Med Chem. 2004; 12:5587-93). Furthermore, it has also been shown that intragastric administration of pro-EGCG in CF-1 mice results in better bioavailability than with administration of equimolar doses of EGCG (Lambert J D, et al. Drug Metab Dispos 2006; 34, 2111-6).

As used herein, "endometriosis and related indication" refers to endometriosis or adenomyosis, and any medical disorders and conditions caused by, or associated with endometriosis directly or indirectly. In exemplary applications the type of endometriosis is peritoneal or pelvic endometriosis.

As used herein, "treatment" refers to prevention, alleviation or amelioration of any clinical presentations and outcomes of endometriosis or a disorder or condition associated with endometriosis.

Anti-angiogenesis is one of the most well-characterized biological properties of green tea polyphenols. Experimental studies using a variety of tumor angiogenesis models have shown that green tea extract and EGCG in particular have potent anti-angiogenic effects (Fassina G, et al. Clin Cancer Res 2004; 10:4865-73; Liao J, et al. Nutr Cancer 2004; 48:44-53).

The underlying mechanism is still not fully understood, although the inhibitory effects of EGCG on VEGF expression and on receptor activity in cancer, as well as in endometriosis, have been extensively investigated (Xu H, et al. Fertil Steril 2011; 96:1021-8; Lamy S, et al. Cancer Res 2002; 62:381-5; Kojima-Yuasa A, et al. Life Sci 2003; 73:1299-313; Kondo T, et al. Cancer Lett 2002; 180:139-44; Jung Y D, et al. Br J Cancer 2001; 84:844-50; Sartippour M R, et al. J Nutr 2002; 132:2307-11).

In the examples detailed below in the present invention, pro-EGCG showed stronger and better anti-angiogenic effects than natural EGCG on the experimental endometriosis model in mice.

Because pro-EGCG has higher plasma and tissue anti-oxidation and anti-angiogenesis capacities than EGCG, the enhanced bioactivity of pro-EGCG in the endometriosis model might have been due to its better bioavailability in vivo.

Although the anti-angiogenesis mechanism of pro-EGCG was not investigated in the present study, similar inhibitory effects on VEGF expression and receptor activity could be expected. EGCG and pro-EGCG are also potent anti-oxidants. EGCG and pro-EGCG significantly increased their total anti-oxidation capacities in plasma and lesions, as did Vitamin E, but vitamin E had no effects on endometriotic angiogenesis and growth, suggesting that the anti-angiogenic effects of pro-EGCG on experimental endometriosis were independent from its anti-oxidative properties.

Pro-EGCG exhibited proteasome inhibition and cell death induction in cancer cells (Lam W H, et al. Bioorg Med Chem. 2004; 12:5587-93). Pro-EGCG showed much higher potency than EGCG in the inhibition of proliferation and transforming activity and the induction of apoptosis in human prostate, breast, leukemic, and simian virus 40-transformed cells (Kuhn 1), et al. Front Biosci 2005; 10:1010-

23). In experimental endometriosis, pro-EGCG induced more cell death than EGCG in the developing endometriotic lesions.

In the examples detailed below, pro-EGCG also demonstrated greater efficacy than EGCG in the inhibition of the development and growth of experimental endometriosis in mice.

It has been demonstrated that bioluminescence was strongly correlated with lesion size from the first week (Becker C M, et al. Am J Pathol 168:2074-2084). The significant decrease in bioluminescence after 2 weeks of pro-EGCG treatment is considered to be evidence of the efficacy of pro-EGCG in the inhibition of the development and growth of endometriosis in mice. Although EGCG also significantly inhibited the lesion growth from 2 weeks, the inhibitory effects of pro-EGCG were unexpectedly more potent than that of EGCG throughout the treatment. In contrast to the prostate cancer inoculation model in mice (Lee S C, et al. Nutr Cancer 2008; 60:483-91), the significant inhibition of endometriotic growth in our study was observed after 2 weeks of pro-EGCG treatment, while the inhibition of tumor growth in Lee's study was observed as early as in the 1st week of treatment. The delayed efficacy might have been due to the larger tissues (5 pieces in 2 $mm^3$ each) used in this study compared to the single piece of 1 $mm^3$ used in Lee's study.

Unfortunately, due to technical limitations we did not monitor the microvessels at different time points directly; therefore, we cannot exclude whether inhibition is associated with a reduction of blood vessels in the lesions.

As noted in the background section, current treatments for endometriosis consist of various hormonal therapies aimed at interrupting the cycles of stimulation and bleeding of endometriotic lesions. However, this approach is deemed not very satisfactory (Rice V M. Ann N Y Acad Sci 2002; 955:343-52).

There also exist major issues with the use of thalidomide (a potential teratogen), despite results showing promising pain relief in endometriosis patients. Furthermore, anti-angiogenic agents could also serve to limit physiological angiogenesis, such as in ovulation and menstruation (Nyberg P, et al. Cancer Res 2005; 65:3967-79). These agents' possible adverse effects on reproductive functions and on offspring must be addressed in this vulnerable population (Klauber N, et al. AGM-1470. Nat Med 1997; 3:443-6; Becker C M, et al. Fertil Steril 2005; 84 Suppl 2:1144-55).

In the examples detailed below, it was demonstrated that ovarian follicles and uterine endometrial glands were not affected by either EGCG or pro-EGCG treatment, suggesting these natural anti-angiogenic agents might not alter normal ovulation and menstruation.

Pro-EGCG can be easily manufactured at a relatively low cost and might already have a toxicity profile similar to that of EGCG (Can Y H, et al. Nutr Biochem 2002; 13:380-90).

Pharmaceutical Formulations

Pro-EGCG of the present invention can be administrated alone, or more preferably, formulated with conventional carriers and excipients which can be appropriately selected by a person skilled in the art. The formulations of the invention comprise Pro-EGCG, together with one or more pharmaceutically acceptable carriers and optionally other therapeutic ingredients.

An effective amount of Pro-EGCG is contained in the formulations to achieve the intended purpose. More specifically, a therapeutically effective amount means an amount of Pro-EGCG effective to prevent, alleviate or ameliorate clinical presentations and outcomes of endometriosis or a disorder or condition associated with endometriosis.

Formulations of the present invention may be presented as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion, and may be prepared according to any method known to the art.

Pharmaceutical formulations containing the active ingredient may be provided in any form suitable for the intended method of administration, including (but not limited to) enteral administration, parenteral administration (including peritoneal administration, intravenous administration), and topical administration. In a preferred embodiment, the formulation is administered to the uterine cavity or vagina of a female subject in need of treatment.

Specific dosage amount and interval of administration may be determined and adjusted by a person skilled in the art based upon the needs of individual recipients to provide the required plasma levels of Pro-EGCG.

Additional objects, advantages, and novel features of the present invention will become apparent to a person skilled in the art upon consideration of the following examples, which are not intended to be limiting.

EXAMPLES

Overview

Homologous endometrium was subcutaneously transplanted into mice to receive either saline, vitamin E, EGCG or pro-EGCG treatment for 4 weeks. The growth of the endometrial implants was monitored by IVIS® non-invasive in vivo imaging during the interventions. Angiogenesis of the endometriotic lesions was determined by Cellvizio® in vivo imaging and SCANCO® Microfil microtomography. The bioavailability, anti-oxidation and anti-angiogenesis capacities of the treatments were measured in plasma and lesions. The implants with adjacent outer subcutaneous and inner abdominal muscle layers were collected for histo¬logical, microvessel and apoptosis examinations.

Material and Methods

Chemicals

Pro-EGCG was synthesized from (−)-EGCG by treating the (−)-EGCG with acetic anhydride and pyridine overnight, as previously described (Lam W H, et al. Bioorg Med Chem. 2004; 12:5587-93). HPLC-graded EGCG, vitamin E and solvents were purchased from Sigma-Aldrich (St. Louis, Mo.). D-Luciferin (Caliper Life Sciences, MA), FITC-Dextran MW150,000 (PolySciences Inc., PA), YO-PRO®-1 iodide (Invitrogen, CA) and Microfil MV-120 Blue (Flow Tech, MA), used for in vivo imaging, were purchased from their respective manufacturers.

Animals

Transgenic luciferase-expressing mice (CMV-Luc) were obtained from Xenogen (Xenogen Cor., CA), and immunocompromised mice (NOD-SCID) were obtained from Jackson Laboratory (Bar Harbor, Me.). All animals were housed in disease free conditions in a separate barrier facility with individually ventilated filter cages at university hospital. Ambient temperature was monitored and cycles of light and darkness were regulated. Mice were fed with irradiated laboratory chow and sterile water ad libitum for at least one week of acclimatization before the surgery and experiments. All of the animal research was approved from the Animal Experimentation Ethics Committee (07/010/MIS) and was performed in accordance with the institutional guidelines.

Experimental Endometriosis

Based on our previous study, an immune-compromised mouse model of experimental endometriosis was created by subcutaneous transplantation of human or mouse tissues to assess the anti-angiogenic effects and mechanisms of green tea catechin (Xu H, et al. Hum Reprod 2009; 24:608-18; Xu H, et al. Fertil Steril 2011; 96:1021-8). Either subcutaneous or intraperitoneal inoculations of the endometrial tissues in mice effectively resulted in the formation of endometriotic lesions at both locations (Nap A W, et al. J Clin Endocrinol Metab 2004; 89:1089-95), but subcutaneous implantation allowed for more accurate quantification of size and number of the lesions and also easy access for in vivo imaging.

In this study, endometrial tissues from eight-week-old female CMV-Luc mice (n=15) were acquired for transplantation into nonluminescent NOD-SCID mice (n=32). The mouse endometrium was obtained during the proliferating estrous stage, and biopsies 2 mm in diameter were obtained with a sterile dermal biopsy punch (Miltex, N.Y.). The biopsies were immediately washed in prewarmed, phenol-red-free DMEM/F-12 medium (Sigma) to remove residual blood and mucus, and the samples were maintained in serum-free DMEM/F-12 medium before transplantation (Bruner-Tran K L, et al. J Clin Endocrinol Metab 2009; 94:2489-94). Cultured endometrial biopsies were randomly allocated for transplantation.

Five mouse endometrial biopsies per treatment group were implanted into a single subcutaneous pocket created in the abdominal wall of the mice along the ventral midline immediately below the umbilicus. All of the surgical procedures were performed under general anesthesia with isoflurane (Baxter, Ill.), and the mice were monitored until they fully recovered.

Immediately after the transplantation, the mice were randomly assigned to receive either vehicle (n=8; sham control), vitamin E (n=8; anti-oxidant control, 20 mg/kg), EGCG (n=8; anti-angiogenesis control, 50 mg/kg, ≈1.5 mg/30 g) or pro-EGCG (n=8; 50 mg/kg).

Dulbecco's phosphate-buffered saline (PBS, Sigma) was used as solvent to dissolve the drugs. These doses were selected because their significant anti-angiogenic and anti-oxidative effects have been reported in mice (Sang S, et al. Chem Res Toxicol 2005; 18, 1762-9; Villayandre B M, et al. Brain Research 2004; 1028, 148-55). The treatments were administered once per day via intraperitoneal injections for a consecutive 4-week period.

At the end of intervention, size of the endometriotic lesions was determined as the longest length and perpendicular width according to a venire caliper and was calculated as $0.52 \times width^2 \times length$ in $mm^3$. The endometrial implants, together with subcutaneous and muscle layers, were removed from the abdomen wall for detailed histological examination and specific staining analysis.

In Vivo Imaging

Development and angiogenesis of the experimental endometriosis were monitored using various in vivo imaging systems. During the intervention, growth of the endometriotic lesions (n=8 per group) was monitored each week by measuring the bioluminescence of the subcutaneous luciferase-positive implants using a non-invasive IVIS 200 live animal imaging system (Xenogen) as previously described (Song C, et al. Hum Gene Ther. 2011; 22:439-49). A total of 150 mg/kg of luciferin was injected intraperitoneally into the mouse tail vein 10 mins prior to imaging. An image from each animal was captured at bin size 4 in triplicate, and the bioluminescence signal intensities were averaged for comparison.

At the end of intervention, functional angiogenesis of the endometriotic lesions (n=8 per group) was monitored by measuring the flow of fluorescence dye in the new microvessels developed in the implants using a Cellvizio® LAB LSU-488 system with a ProFlex Microprobe S1500 (Mauna Kea Technologies, Paris) as previously described (Xu H, et al. Fertil Steril 2011; 96:1021-8). A total of 10 mg/ml of FITC-Dextran was injected intravenously into each mouse prior to imaging. Total vessel length (μm) and area (μm$^2$) and functional capillary length (μ$^{-1}$) and area density were measured using Cellvizio® LAB Vessel Detection software, and averaged from 4 perpendicular regions of the lesions in replicates. At the same time, apoptotic cells in the lesions were captured by Cellvizio-LAB 488 with a ProFlex MiniO/100 microprobe using Cellvizio® LAB I/C Viewer software (Mauna Kea Technologies). A total of 10 μl of 10 μM YO-PRO®-1 iodide in DSMO was injected directly into the lesion area.

The total number of apoptotic cells was counted and averaged from the 4 perpendicular regions of the lesions in replicates as described above. Both IVIS and Cellvizio imaging procedures were performed under general anesthesia with isoflurane (Baxter, Ill.), and the mice were observed until fully recovered.

After live animal imaging, structural angiogenesis in the endometriotic lesions (n=4 per group) was further examined by detecting the Microfil in the new microvessels developed in the implants using a VivaCT 40 μCT system (Scanco Medical, Switzerland) as previously described (Sun M H, et al. J Orthop Res. 2012; 30:137-43). The mice were sacrificed by cervical dislocation and were immediately perfused with 4% paraformaldehyde and Microfil MV-120 Blue. Three-dimensional microvessel architecture was constructed, and absolute and relative Microfil-filled microvessel volumes were determined using the built-in software.

Histology and Immunostaining

Paraffin sections (n=4 per group) were prepared for standard hematoxylin and eosin (H&E) staining, angiogenesis immunostaining and TUNEL staining as previously described (Xu H, et al. Hum Reprod 2009; 24:608-18). Immunohistochemistry staining of in situ angiogenesis was performed by the immunoperoxidase method using a MACH 3 HRP Polymer Kit (Biocare Medical, Concord), and counterstained using methyl green or blue solution.

Antibodies against mouse CD31 and alpha-smooth muscle actin (αSMA) (Abeam Inc., MA) were used to double fluorescence stain the microvessels developed in the endometriotic lesions, and CD34 (Abeam Inc.) was used to stain the microvessels in the ovaries and uterus. The samples without primary antibodies served as negative controls. The total number of positively stained new and old microvessels in the lesions was counted, respectively. The mean microvessel numbers and sizes were calculated from 5 separated sections from each animal within the treatment group and are presented as numbers per lesion and μm$^2$ per lesion, respectively.

TUNEL labeling for in situ apoptotic cells was performed using an ApopTag Peroxidase In Situ Apoptosis Detection Kit (Temecula, Calif.) according to the manufacturer's instructions. The total numbers of TUNEL-positive stained cells were counted. The mean numbers of apoptotic cells were calculated from 5 separated sections from each animal within the treatment group and are presented as numbers per lesion as above. For all of the examinations, five best sections showed complete histological features of the outer skin and subcutaneous layers; the middle endometriotic lesion and the inner abdominal muscles and peritoneum were first evaluated and were selected for detailed examination by two experienced pathologists. Each section was evaluated by both examiners, who were blinded to the experimental groups and results.

Analytical Measurements

Pharmacokinetics of EGCG and pro-EGCG in the animals were studied by measuring the corresponding EGCG and pro-EGCG concentrations (EGCG in the EGCG group, pro-EGCG in the pro-EGCG group) in plasma during the intervention and also in lesions at the end of intervention. EGCG and pro-EGCG were quantified by analytical methods as previously described (Lam W H, et al. Bioorg Med Chem. 2004; 12:5587-93; Chu K O, et al. J Chromat B 2004; 810:187-95; Chu K O, et al. Anal Chim Acta 2004; 510:69-76). Anti-oxidative and anti-angiogenesis capacities of the samples were also studied by measuring oxygen radical absorbance capacity (ORAC) using a modified phycoerythrin fluorescence decay assay as previously described (Wang C C, et al. Clin Chem 2004; 50:952-4), and vascular endothelial growth factor (VEGF) concentrations were measured using a commercial ELISA kit (Uscn Life Science Inc., TX) according to the manufacturer's manual. Blood samples (n=8 per group) were collected from the tail vein once per week, and plasma was prepared by immediate centrifugation. Implants without subcutaneous and muscle layers (n=4 per group) were removed from the abdominal wall, and the endometriotic lesions were frozen. All of the samples were kept in −80° C. prior to analysis.

Eutopic Endometrium and Ovary

Reproductive effects of EGCG and pro-EGCG on the endometrium and ovaries of each animal were also examined. After the 4-week intervention, the uterine horns and ovaries (n=8 per group) were removed and fixed for histological examination and angiogenesis immunostaining as described above. Endometrial glands, ovarian follicles and vascularization in endometrial and ovarian stroma were assessed.

Statistics

Sample size for animals was calculated according to standard methods and as described in our previous studies (Xu H, et al. Hum Reprod 2009; 24:608-18). The anticipated difference in reduced size in the experimental endometriotic lesions after EGCG treatment in mice was 10 mm$^2$, and the anticipated standard deviation was 3.5 mm$^2$, so at least 8 mice per treatment group were required for a type I error of 0.01 with power of 99%. The results are expressed as means±SEMs. Longitudinal comparisons between the groups during the intervention were performed using ANOVA followed by post hoc comparisons of individual groups using Bonferroni correction. Final comparisons between the groups after the intervention were performed using Student's parametric independent t-test. Statistical analysis was performed with PASW Statistics version 18 (SPSS Inc., IL). P values <0.05 were considered to be significant.

Results

Pro-EGCG Suppresses the Growth of Experimental Endometriosis in Mice

Figure 1A:
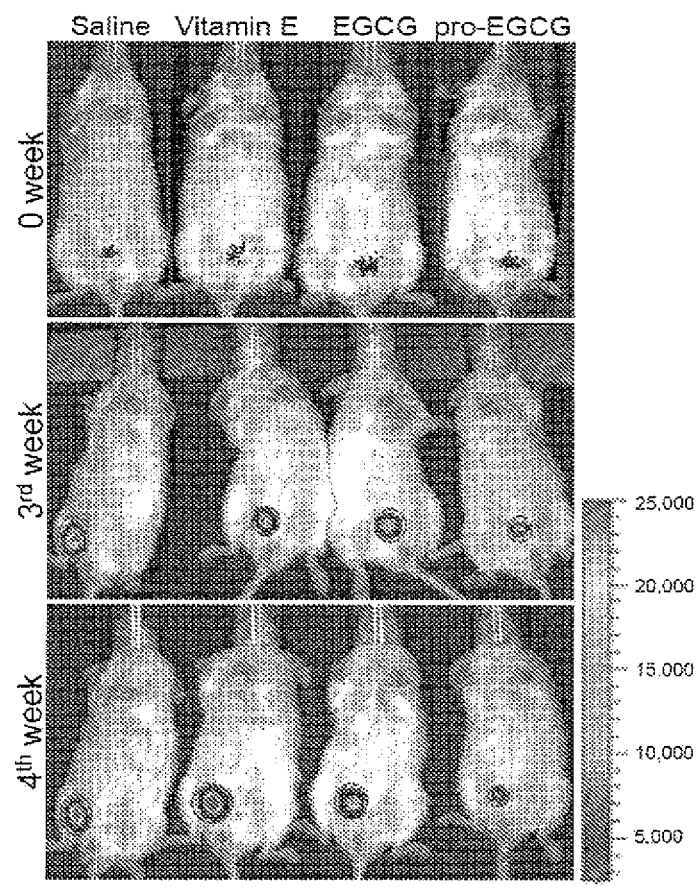
FIG. 1A shows luminescent signals from implants measured at baseline (0 week), 3 week and 4 week. The intensity of the luminescent signal denotes as in a color scale extending from luminescence intensity of 0 (blue, low signal, no growth), 15,000 (green, moderate signal, slow growth) to 25,000 (red, high signal, fast growth).

The endometriotic lesions were monitored with non-invasive in vivo imaging to determine the therapeutic effects of pro-EGCG on the growth and development of experimental endometriosis in mice. Growth of the luminescent endometriotic lesions was monitored in every week during interventions, and was indicated by the increased bioluminescent signals from the implants (FIG. 1A).

Figure 1B:
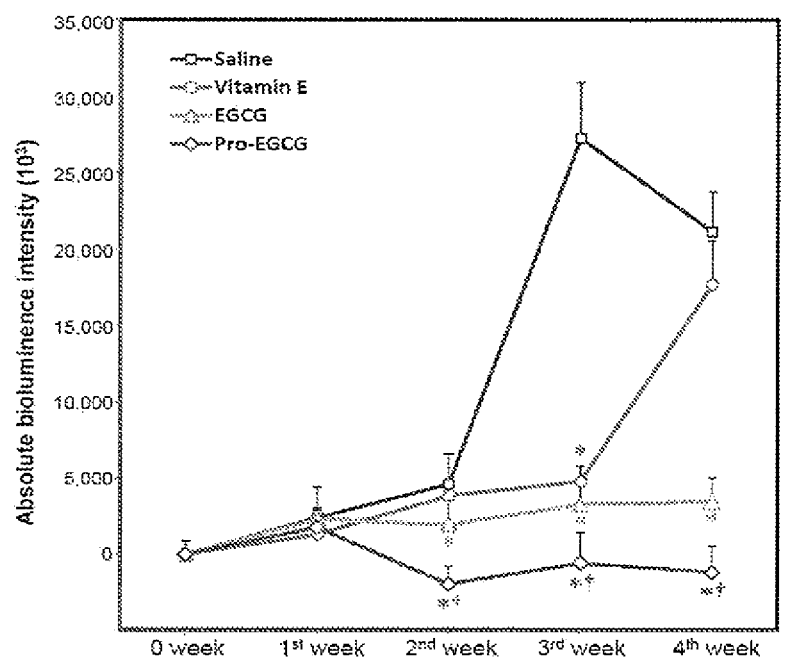
FIG. 1B shows the longitudinal changes of absolute luminescence intensities recorded in every week during interventions. Mean±SEM, On-way ANOVA and multiple comparisons by post hoc Bonferroni test, *$P<0.05$ compared with saline group; †$P<0.05$ compared with EGCG group.

In the control saline group, the lesion bioluminescence was slightly increased in the first 2 weeks; then it rapidly increased at the 3rd week and maintained at high levels at the 4th week (FIG. 1B).

With EGCG treatment, the lesion bioluminescence was maintained around the baseline levels, and the intensity was significantly lower than that of the saline group at the 2nd, 3rd and 4th weeks of the intervention.

With pro-EGCG treatment, the lesion bioluminescence decreased further below the baseline levels, and the intensity was significantly lower than that of both the saline group and the EGCG group at the 2nd, 3rd and 4th weeks of the intervention.

In the vitamin E group, the lesion bioluminescent intensity was significantly lower than that of the saline group at the 3rd week, but it returned to normal growth, as in the saline group, at the 4th week of the intervention.

Pro-EGCG Limits the Development of Experimental Endometriosis in Mice

Figure 2A:
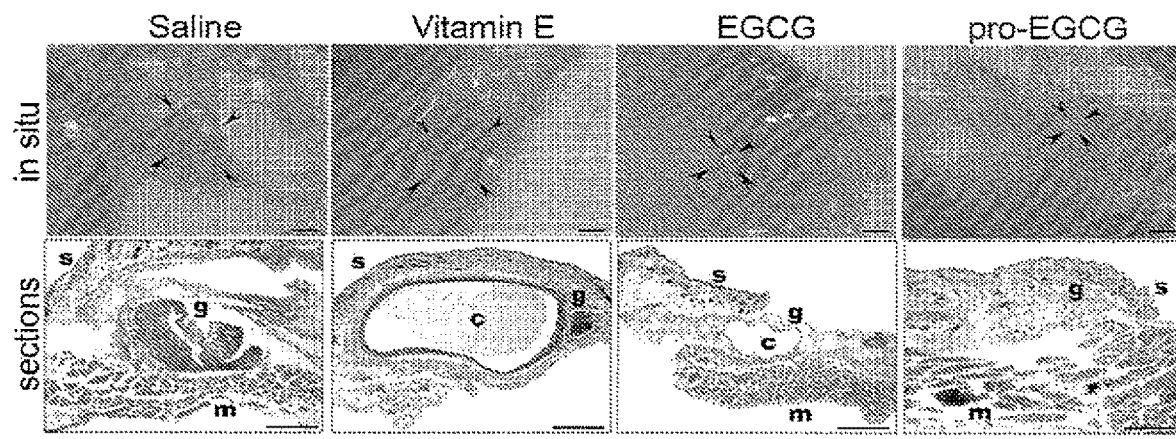
FIG. 2A shows at the upper panels the endometrial implants developed in the right ventral abdominal wall under laparotomy (Arrows indicate the greatest length and perpendicular width of the lesions for lesion size calculation); and at the lower panels the sandwich structures of the developing endometriotic lesions, including outer skin and subcutaneous layers (s), middle endometriotic lesions with endometrial glands (g) and endometrial cyst-like structures (c), and inner abdominal muscle and peritoneum (m). Scale bars: 0.5 mm.

At the terminal surgery, the implanted endometriotic lesions were identified as being located between the host abdominal muscle and the subcutaneous layers (FIG. 2A). The lesions were smooth and well-defined. Under microscopic examination, the lesions were situated between the inner abdominal muscle and the peritoneal layers and the outer subcutaneous and skin layers.

Figure 2B:
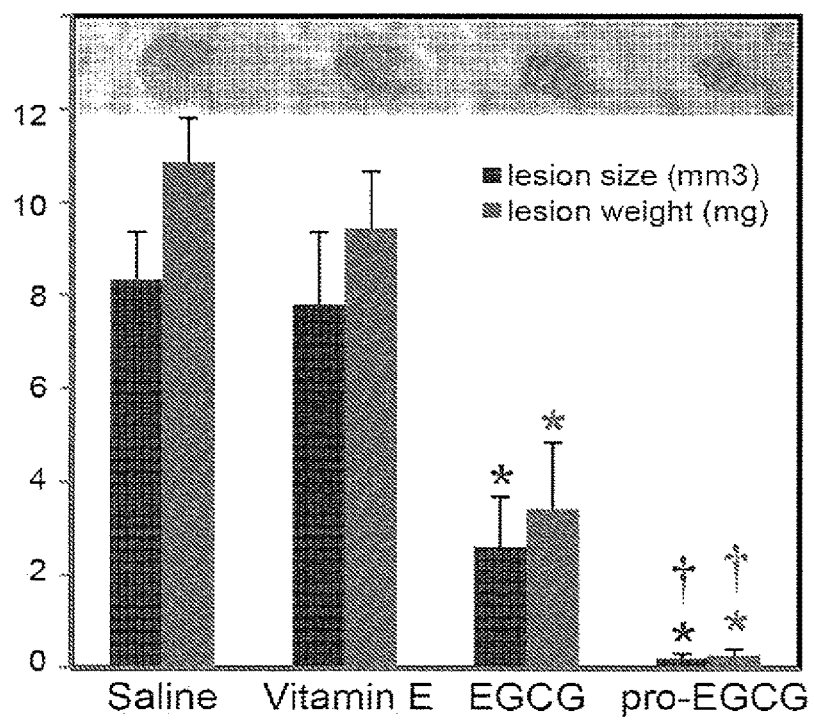
FIG. 2B shows bar charts of the lesion size and weight in different groups and representative lesion pictures. Mean±SEM, Student's T test, *$P<0.05$ compared with saline group; †$P<0.05$ compared with EGCG group.

Compared to the control group, the lesion size and weight were significantly decreased in both the EGCG and pro-EGCG groups (FIG. 2B). The lesions from the pro-EGCG treated mice were significantly smaller and lighter than the lesions from the EGCG-treated mice. The endometriotic lesions after EGCG and pro-EGCG treatment were poorly developed.

The endometrial tissues were small and loosely attached to the adjacent tissues in the EGCG group but were degraded and almost detached from the peritoneal muscle layers in the pro-EGCG group. In contrast, systemic treatment with vitamin E did not significantly decrease the lesions' size or weight, and a large cyst-like endometrial gland structure was formed.

Pro-EGCG Inhibits the Angiogenesis of Experimental Endometriosis in Mice

In vivo angiogenesis imaging by Cellvizio and microCT and in situ angiogenesis immuno-histochemistry analysis by CD31 and αSMA staining showed that lesion neovascularization was poorly developed in the EGCG- and pro-EGCG-treated mice (FIG. 3A). When compared to the saline group, both EGCG and pro-EGCG, but not vitamin B, significantly inhibited the total vessel length and area, the functional capillary length, density and area, the vessel volume and density, and both the CD31-positively and αSMA-negatively stained new microvessel numbers and the CD31-positively and αSMA-positively stained old microvessel numbers in the lesions (FIG. 3B). All of the microvessel parameters in the pro-EGCG group were significantly lower than those in the EGCG group.

Pro-EGCG Enhances the Apoptosis of Experimental Endometriosis in Mice

In vivo apoptosis imaging by Cellvizio and in situ dUTP nick end labeling by TUNEL staining showed that lesion apoptosis increased in the EGCG- and pro-EGCG-treated mice (FIG. 4A). Compared to the saline group, both EGCG and pro-EGCG but not vitamin E significantly increased the total apoptotic cell numbers in the lesions (FIG. 4B). The apoptotic cell numbers in the pro-EGCG group were also significantly higher than the number in the EGCG group.

High bioavailability, anti-oxidation and anti-angiogenesis capacities of Pro-EGCG The EGCG and pro-EGCG concentrations and the ORAC and VEGF concentrations (i) in plasma during the intervention and (ii) in endometriotic lesions after the intervention were measured to compare the pharmacokinetics and the anti-oxidation and anti-angiogenesis capacities of the treatment in mice.

The bioavailability of the treatment in plasma and in endometriotic lesions with pro-EGCG was significantly higher than that with EGCG (FIG. 5A). ORAC in plasma and endometriotic lesions significantly increased in the vitamin E, EGCG and pro-EGCG groups compared to the saline group (FIG. 5B).

ORAC in plasma and endometriotic lesions in the pro-EGCG group was significantly higher than in the EGCG and vitamin E groups, but the EGCG group was not significantly different from the vitamin E group.

VEGF concentrations in plasma and endometriotic lesions significantly decreased in the EGCG and pro-EGCG groups compared to the saline group, while the vitamin E group was not significantly different from the saline group (FIG. 5C). VEGF concentrations in plasma and endometriotic lesions in the pro-EGCG group were significantly lower than those in the EGCG group.

Pro-EGCG Preserves Normal Ovarian Follicles and Endometrial Glands

All of the animals were healthy and active after the endometrium transplantation. No signs of stress, intolerance to anesthesia, surgery or implantation or any toxic responses to saline, vitamin E, EGCG and pro-EGCG administration were observed during the interventions. No significant changes in weight were observed over the experimentation period within and among the groups. There was no observable swelling, inflammation or hair loss at the abdominal implantation sites.

Ovarian follicles and endometrial glands were determined by H&E staining and microvessels in ovarian and endometrial stroma were determined by anti-mouse CD34 immunostaining in ovaries. The histological examination revealed no obvious reproductive effects on ovarian follicles (FIG. 6A) and endometrial glands (FIG. 6B). Also, vascularization of the ovaries and the uterus was not affected in any of the treatment groups.

CONCLUSION

Pro-EGCG significantly inhibited the development, growth and angiogenesis of experimental endometriosis in mice with greater efficacy, better bioavailability, and greater anti-oxidation and anti-angiogenesis capacities than EGCG. Pro-EGCG is anticipated to be a potent anti-angiogenesis agent for endometriosis.

The present invention provides an improved method of treating endometriosis and related indications comprising the administration of Pro-EGCG, a synthetic derivative of epigallocatechin-3-gallate (−)-EGCG, which is associated with enhanced stability and improved bioavailability. Importantly, the use of Pro-EGCG in an improved method of treating endometriosis and related indications does not impact upon physiological angiogenesis, such as in ovulation and menstruation, in the treated female subjects, and the method is free from side effects on reproductive functions, in contrast to other approaches which may be currently utilised.

Additionally, Pro-EGCG when used in an improved method of treating endometriosis and related indications involves the use of an easily manufactured compound, which may be produced at relatively low cost.

The invention claimed is:

1. A method of treating endometriosis or a related indication free from side effects on reproductive functions, said method comprising administering to a subject in need thereof an effective amount of Pro-EGCG having the formula:

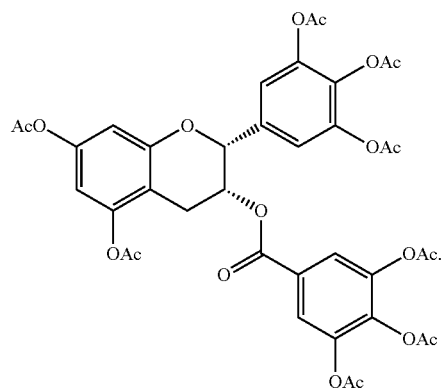 [SMILES: CC(=O)Oc1cc(OC(C)=O)c2c(c1)O[C@H](c1cc(OC(C)=O)c(OC(C)=O)c(OC(C)=O)c1)[C@H](OC(=O)c1cc(OC(C)=O)c(OC(C)=O)c(OC(C)=O)c1)C2]

2. The method of claim 1, wherein said method does not affect vascularization of the ovaries and uterus of the subject.

3. The method of claim 1, wherein said method has no obvious reproductive effects on the ovarian follicles and endometrial glands of the subject.

4. The method of claim 1, wherein said method is a method of treating endometriosis.

5. The method of claim 1, wherein said endometriosis is peritoneal or pelvic endometriosis.

6. The method of claim 1, wherein said method is a method of treating adenomyosis.

7. The method of claim 1, wherein said effective amount of Pro-EGCG is 50 mg/kg.

8. The method of claim 1, wherein said Pro-EGCG is administered to said subject once a day via intraperitoneal injection.

9. The method of claim 1, wherein said Pro-EGCG is administered to said subject once a day via intraperitoneal injection for a consecutive 4-week period.

10. The method of claim 1, wherein the method inhibits angiogenesis in endometriosis.

11. The method of claim 1, wherein the method enhances apoptosis in endometriotic lesions.

12. The method of claim 1, wherein the method increases the bioavailability of Pro-EGCG in plasma and endometriotic lesions.

13. The method of claim 1, wherein the method results in a significantly higher oxygen radical absorbance capacity (ORAC) in plasma and endometriotic lesions as compared to treatment using vitamin E or EGCG.

14. The method of claim 1, wherein the method decreases the concentration of vascular endothelial growth factor (VEGF) in plasma and endometriotic lesions.

15. The method of claim 1, wherein the method does not affect normal ovarian follicles and endometrial glands.

16. The method of claim 1, wherein Pro-EGCG is administered to the subject via enteral or intraperitoneal administration, or an injection into the vagina or uterine cavity.

17. The method of claim 16, wherein said enteral administration is oral administration.

\* \* \* \* \*